US005877288A

United States Patent [19]
Townes et al.

[11] Patent Number: 5,877,288
[45] Date of Patent: Mar. 2, 1999

[54] ANTI-SICKLING HEMOGLOBIN

[75] Inventors: Tim M. Townes; Steven L. McCune, both of Birmingham, Ala.

[73] Assignee: The UAB Research Foundation, Birmingham, Ala.

[21] Appl. No.: 261,664

[22] Filed: Jun. 17, 1994

Related U.S. Application Data

[63] Continuation-in-part of Ser. No. 80,664, Jun. 21, 1993, abandoned.

[51] Int. Cl.$^6$ .................................................. C07K 14/805
[52] U.S. Cl. ............................................................ 530/385
[58] Field of Search .......................... 435/69.1; 530/350, 530/385; 536/22.1, 23.1, 23.5

[56]   References Cited

PUBLICATIONS

Adachi and Asakura, "Nucleation–controlled Aggregation of Deoxyhemoglobin S," The Journal of Biological Chemistry, 254:7765–7771, 1979.
Adachi and Asakura, Separation of asymmetrical hybrid hemoglobins by hydrophobic interaction chromatography, Journal of Chromatography, 419:303–307, 1987.
Adachi, et al., "Nucleation–controlled Aggregation of Deoxyhemoglobin S," The Journal of Biological Chemistry, 255:7595–7603, 1980.
Anderson, "Prospects for Human Gene Therapy," Science, 226:401–409, 1984.
Anderson, "Human Gene Therapy," Science, 256:808–813, 1992.
Antoniou and Grosveld, "β–Globin dominant control region interacts differently with distal and proximal promoter elements," Genes Dev. 4:1007–1013, 1990.
Behringer, et al., "Synthesis of Functional Human Hemoglobin in Transgenic Mice," Science 245:971–973, 1989.
Benesch, et al., "α–Chain Mutations with Opposite Effects on the Gelation of Hemoglobin S," The Journal of Biological Chemistry, 254:8169–8172, 1979.
Bodine, et al., "Combination of interleukins 3 and 6 preserves stem cell function in culture and enhances retrovirus–mediated gene transfer . . . ," Proc. Natl. Acad. Sci. USA 86:8897–8901, 1989.
Bowman, et al., "Hemoglobin G$_{Coushatta}$: A Beta Variant With A Delta–Like Substitution," Biochemical and Biophysical Research Communications, 26:466–470, 1967.
Brimhall, et al., "Two New Hemoglobins," Biochimica et Biophysica Acta, 379:28–32, 1975.
Brinster, et al., "Factors affecting the efficiency of introducing foreign DNA into mice by microinjecting eggs," Proc. Natl. Acad. Sci. USA, 82:4438–4442, 1985.
Brittenham, et al., "Hemoglobin S Polymerization: Primary Determinant of the Hemolytic and Clinical Severity of the Sickling Syndromes," Blood, 65:183–189, 1985.
Bunn, "Subunit Assembly of Hemoglobin: An Important Determinant of Hematologic Phenotype," Blood, 69:1–6, 1987.

Caterina, et al., "Human β–globin locus control region: Analysis of the 5' DNase I hypersensitive site HS 2 in transgenic mice," Proc. Natl. Acad. Sci. USA, 88:1626–1630, 1991.
Crepeau, et al., Diameter of haemoglobin S fibres in sickled cells, Nature, 274:616–617, 1978.
Dykes, et al., "Three–dimensional Reconstruction of the 14–Filament Fibers of Hemoglobin S," J. Mol. Biol., 130:451–472, 1979.
Eaton and Hofrichter, "Hemoglobin S Gelation and Sickle Cell Disease," Blood, 70:1245–1266, 1987.
Edelstein, "Molecular Topology in Crystals and Fibers of Hemoglobin S," J.Mol. Biol., 150:557–575, 1981.
Eglitis and Anderson, "Retroviral Vectors for Introduction of Genes into Mammalian Cells," BioTechniques, 6:608–614, 1988.
Friedmann, "Progress Toward Human Gene Therapy," Science, 244:1275–1281, 1989.
Glover, "Gene Cloning The Mechanics of DNA Manipulation," Brammer and Edidin, eds. (Chapman and Hall, New York) pp. 20–47, 1984.
Hofrichter, et al., "Kinetics and Mechanism of Deoxyhemoglobin S Gelation: A New Approach to Understanding Sickle Cell Disease," Proc. Natl. Acad. Sci. USA, 71:4864–4868, 1974.
Ingram, "A Specific Chemical Difference Between the Globins of Normal Human and Sickle–Cell Anaemia Haemoglobin," Nature, 178:792–794, 1956.
Ingram, "Gene Mutations in Human Haemoglobin: The Chemical Difference Between Normal and Sickle Cell Haemoglobin," Nature, 180:326–328, 1957.
Ip and Asakura, "Separation of Asymmetrical Hybrid Containing Hemoglobin F by Anaerobic Anion–Exchange High–Performance Liquid Chromatography," Analytical Biochemistry, 156:348–353, 1986.
Kaufman, et al., "Haemoglobin G–Szuhu, β–80 Asn–lys, in the Homozygous State in a Patient with Abetalipoproteinaemia," Hum. Hered. 25:60–68, 1975.
Lau, et al., "Versatile cosmid vectors for the isolation, expression, and rescue of gene sequences: Studies with the human α–globin gene cluster," Proc. Natl. Acad. Sci. USA 80:5225–5229, 1983.
Lewis and Thompson, "Efficient site directed in vitro mutagenesis using ampicillin selection," Nucleic Acids Research, 18:3439–3443, 1990.
Markowitz, et al., "Construction and Use of a Safe and Efficient Amphotrophic Packaging Cell Line," Virology, 167:400–406, 1988.
Markowitz, et al., "A Safe Packaging Line for Gene Transfer: Separating Viral Genes on Two Different Plasmids," Journal of Virology, 62:1120–1124, 1988.

(List continued on next page.)

*Primary Examiner*—Keith D. Hendricks
*Assistant Examiner*—Karen Cochrane Carlson
*Attorney, Agent, or Firm*—Clark & Elbing LLP

[57]   ABSTRACT

Disclosed are anti-sickling human hemoglobins for use as sickle cell anemia therapeutics.

16 Claims, 11 Drawing Sheets

OTHER PUBLICATIONS

Miller and Rosman, "Improved Retroviral Vectors for Gene Transfer and Expression," BioTechniques, 7:980–990, 1989.

Miller and Buttimore, "Redesign of Retrovirus Packaging Cell Lines to Avoid Recombination Leading to Helper Virus Production," Molecular and Cellular Biology, 6:2895–2902, 1986.

Moo–Penn, et al., "Hemoglobin Presbyterian: β108(G10) Asparagine→Lysine. A Hemoglobin Variant with Low Oxygen Affinity," FEBS Letters, 92:53–56, 1978.

Nagel, et al., "Structural bases of the inhibitory effects of hemoglobin F and hemoglobin $A_2$ on the polymerization of hemoglobin S," Proc. Natl. Acad. Sci. USA, 76:670–672, 1979.

Nagel, et al., "β–Chain contact sites in the haemoglobin S polymer," Nature, 283:832–834, 1980.

Noguchi, et al., "Levels of Fetal Hemoglobin Necessary For Treatment of Sickle Cell Disease," The New England Journal of Medicine, 318:96–99, 1988.

Noguchi and Schechter, "The Intracelluar Polymerization of Sickle Hemoglobin and Its Relevance to Sickle Cell Disease," Blood, 58:1057–1068, 1981.

Padlan and Love, "Refined Crystal Structure of Deoxyhemoglobin S," The Journal of Biological Chemistry, 260:8280–8291, 1985.

Perutz and Lehmann, "Molecular Pathology of Human Haemoglobin," Nature, 219:902–909, 1968.

Prchal, et al., "Mild Sickle Cell Anemia Associated with Alpha Globin Mutant Alpha Montgomery," The American Journal of Medicine, 86:232–236, 1989.

Pursel, et al., "Genetic Engineering of Livestock," Science, 244:1281–1288, 1989.

Ryan, et al., "A single erythroid–specific DNase I super–hypersensitive site activates high levels of human β–globin gene expression in transgenic mice," Genes & Development, 3:314–323, 1989.

Ryan, et al., "Human Sickle Hemoglobin in Transgenic Mice," Science, 247:566–568, 1990.

Watson–Williams et al., "A New Haemoglobin, D Ibadan (β–87 Threonine→Lysine), Producing No Sickle–Cell Haemoglobin D Disease with Haemoglobin S," Nature, 205:1273–1276, 1965.

Shelton, et al., "High Performance Liquid Chromatographic Separation of Globin Chains on a Large–Pore $C_4$ Column," Journal of Liquid Chromatography, 7:1969–1977, 1984.

Ward, et al., "Crystal Structure of Sickle–cell Deoxyhemoglobin at 5 Å Resolution," J. Mol. Biol., 98: 179–194, 1975.

- ● 100% Hb S
- ○ 75% Hb S/25% Hb A
- □ 75% Hb S/25% Hb AS1
- ■ 75% Hb S/25% Hb AS2
- △ 75% Hb S/25% Hb F

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 27
( B ) TYPE: nucleic acid
( C ) STRANDEDNESS: single
( D ) TOPOLOGY: linear ( x i ) SEQUENCE DESCRIPTION: SEQ ID NO: 1:

GTGAACGTGG ATGCCGTTGG TGGTGAG 27

( 2 ) INFORMATION FOR SEQ ID NO: 2:

( i ) SEQUENCE CHARACTERISTICS:
( A ) LENGTH: 27
( B ) TYPE: nucleic acid
( C ) STRANDEDNESS: single
( D ) TOPOLOGY: linear ( x i ) SEQUENCE DESCRIPTION: SEQ ID NO: 2:

GCTCACCTGG ACAAGCTCAA GGGCACC 27

( 2 ) INFORMATION FOR SEQ ID NO: 3:

( i ) SEQUENCE CHARACTERISTICS:
( A ) LENGTH: 27
( B ) TYPE: nucleic acid
( C ) STRANDEDNESS: single
( D ) TOPOLOGY: linear ( x i ) SEQUENCE DESCRIPTION: SEQ ID NO: 3:

GGCACCTTTG CCCAGCTGAG TGAGCTG 27

ANTI-SICKLING HEMOGLOBIN

This application is a continuation-in-part of U.S. Ser. No. 08/080,664, filed Jun. 21, 1993, now abandoned.

BACKGROUND OF THE INVENTION

This invention relates to recombinant anti-sickling hemoglobins suitable for use as therapeutics for the treatment of sickle cell anemia.

The gene that encodes hemoglobin S (the defect leading to sickle cell anemia) is inherited as an autosomal trait and occurs in the heterozygous condition as the sickle trait in 8–10% of black persons in the Unites States. Two major clinical features characterize sickle cell anemia: (1) chronic hemolysis that is stable and only moderately debilitating, and (2) acute, episodic vaso-occlusive crises that cause organ failure and account for most of the mortality and morbidity associated with the disease.

The molecular basis for sickle cell disease is an A to T transversion in the 6th codon of the human β-globin gene. This simple transversion changes a polar glutamic acid residue to a non-polar valine (Ingram et al., Nature 178:792, 1956; Ingram et al., Nature 180:326, 1957) in the β-globin polypeptide and, thus, drastically decreases the solubility of this hemoglobin (termed Hb S). When the intracellular concentration of Hb S is high and the partial pressure of oxygen is low in the capillary beds, the non-polar valine, which is on the surface of the hemoglobin molecule, interacts with two other non-polar residues on the surface of a second hemoglobin molecule, and initiates aggregation (Padlan et al., J. Biol. Chem. 260:8280–8291, 1985; Wishner et al., J. Mol. Biol. 98:179–194, 1975). Once approximately 10 hemoglobin monomers interact, long polymers rapidly accumulate, and complex 14-stranded fibers are formed (Crepeau et al., Nature 274:616–617, 1978; Dykes et al., J. Mol. Biol. 130:451–472, 1979; Eaton et al., Blood 70:1245–1266, 1987; Hofrichter et al., Proc. Natl. Acad. Sci USA 71:4864–4868, 1974). The formation of these fibers reduces the flexibility of red blood cells and leads to the occlusion of small capillaries. Intracellular fiber formation also results in erythrocyte membrane damage and increased red cell lysis (Noguchi et al., Blood 58:1057, 1981; Brittenham et al., Blood 65:183, 1985). The ensuing disease is characterized by a chronic hemolytic anemia with episodes of severe pain, and tissue damage that can result in stroke, kidney failure, heart disease, infection, and other complications (Bunn et al., *Hemoglobin: Molecular, Genetic, and Clinical Aspects.* (W. B. Saunders, Philadelphia, 1986)).

SUMMARY OF THE INVENTION

In one aspect, the invention features recombinant human hemoglobin with anti-sickling activity. Preferably, such anti-sickling hemoglobin is derived from β-globin. In preferred embodiments, the anti-sickling hemoglobin includes a mutation which disrupts the hydrophobic pocket formed by β-globin amino acids phenylalanine 85 and leucine 88, but which leaves intact the correct positioning of the heme moiety. Preferred anti-sickling human hemoglobins include: (a) a glutamine residue at β-globin amino acid 87; (b) a lysine residue at β-globin amino acid 87; (c) a lysine residue at β-globin amino acid 80; (d) an alanine residue at β-globin amino acid 22; (e) a glutamine residue at β-globin amino acid 87 and an alanine residue at β-globin amino acid 22; (f) a lysine residue at β-globin amino acid 87 and an alanine residue at β-globin amino acid 22; (g) a lysine residue at β-globin amino acid 80 and an alanine residue at β-globin amino acid 22; (h) a lysine residue at β-globin amino acid 108; (i) a lysine residue at β-globin amino acid 108 and an alanine residue at β-globin amino acid 22; (j) a lysine residue at β-globin amino acid 108 and a glutamine residue at β-globin amino acid 87; (k) a lysine residue at β-globin amino acid 108 and a lysine residue at β-globin amino acid 87; (l) a lysine residue at β-globin amino acid 108 and a lysine residue at β-globin amino acid 80; (m) a lysine residue at β-globin amino acid 108, an alanine residue at β-globin amino acid 22, and a glutamine residue at β-globin amino acid 87; (n) a lysine residue at β-globin amino acid 108, an alanine residue at β-globin amino acid 22, and a lysine residue at β-globin amino acid 87; (o) a lysine residue at β-globin amino acid 108, an alanine residue at β-globin amino acid 22, and a lysine residue at β-globin amino acid 80; (p) a glutamic acid residue at β-globin amino acid 95; (q) a glutamic acid residue at β-globin amino acid 95 and an alanine residue at β-globin amino acid 22; (r) a glutamic acid residue at β-globin amino acid 95 and a glutamine residue at β-globin amino acid 87; (s) a glutamic acid residue at β-globin amino acid 95 and a lysine residue at β-globin amino acid 87; (t) a glutamic acid residue at β-globin amino acid 95 and a lysine residue at β-globin amino acid 80; (u) a glutamic acid residue at β-globin amino acid 95, an alanine residue at β-globin amino acid 22, and a glutamine residue at β-globin amino acid 87; (v) a glutamic acid residue at β-globin amino acid 95, an alanine residue at β-globin amino acid 22, and a lysine residue at β-globin amino acid 87; (w) a glutamic acid residue at β-globin amino acid 95, an alanine residue at β-globin amino acid 22, and a lysine residue at β-globin amino acid 80; (x) an aspartic acid residue at β-globin amino acid 16; (y) an aspartic acid residue at β-globin amino acid 16 and an alanine residue at β-globin amino acid 22; (z) an aspartic acid residue at β-globin amino acid 16 and a glutamine residue at β-globin amino acid 87; (a') an aspartic acid residue at β-globin amino acid 16 and a lysine residue at β-globin amino acid 87; (b') an aspartic acid residue at β-globin amino acid 16 and a lysine residue at β-globin amino acid 80; (c') an aspartic acid residue at β-globin amino acid 16, an alanine residue at β-globin amino acid 22, and a glutamine residue at β-globin amino acid 87; (d') an aspartic acid residue at β-globin amino acid 16, an alanine residue at β-globin amino acid 22, and a lysine residue at β-globin amino acid 87; (e') an aspartic acid residue at β-globin amino acid 16, an alanine residue at β-globin amino acid 22, and a lysine residue at β-globin amino acid 80. Alternatively, the anti-sickling human hemoglobin may include an arginine residue at a-globin amino acid 48.

The anti-sickling hemoglobin of the invention is preferably encoded by purified DNA, for example, purified DNA which includes a hemoglobin sequence encoding any of the above-listed anti-sickling hemoglobins of the invention.

Finally, the invention features methods for correcting a sickle defect in a mammal by gene therapy. This method involves administering to the mammal a purified nucleic acid encoding a recombinant anti-sickling hemoglobin of the invention, the anti-sickling hemoglobin nucleic acid being positioned for expression in the mammal. In preferred methods, the anti-sickling hemoglobin-encoding nucleic acid is delivered to the mammal as part of a viral vector and is delivered to the mammal's bone marrow. Preferred viral vectors include, but are not limited to retroviral and adeno-associated viral vectors, and any modified versions of these vectors.

The term "recombinant", as used herein, means expressed from an isolated or purified DNA molecule. The recombinant anti-sickling hemoglobins described herein are produced by directed modifications (e.g., by site directed or PCR mutagenesis) of such an isolated DNA molecule.

The term "purified DNA", as used herein, means DNA that is not immediately contiguous with both of the coding sequences with which it is immediately contiguous (i.e., one at the 5' end and one at the 3' end) in the naturally occurring genome of the organism from which the DNA was derived. The term therefore includes, for example, a recombinant DNA molecule which is incorporated into a vector, e.g., an autonomously replicating plasmid or virus, or into the genomic DNA of a prokaryote or eukaryote, or which exists as a separate molecule (e.g., a cDNA or a genomic fragment produced by PCR or restriction endonuclease digestion) independent of other sequences. It also includes a recombinant DNA which is a part of a hybrid gene encoding additional polypeptide sequences.

The term "human hemoglobin", as used herein, means a molecule whose amino acid sequence at least in part corresponds to the amino acid sequence of a naturally-occurring human hemoglobin molecule, whether mutated or wild-type.

The term "anti-sickling", as used herein, means capable of interfering with the aggregation of hemoglobin into 14-stranded hemoglobin molecules characteristic of Hb S hemoglobin and resulting in sickle cell anemia (as described herein). Preferably, the anti-sickling molecules of the invention have approximately the same anti-sickling properties as fetal Hb (i.e., $\alpha_2\gamma_2$) hemoglobin (e.g., as measured by in vitro solubility assays, e.g., the assay of Benesch et al., J. Biol. Chem. 254:8169, 1979).

The term "Hb S hemoglobin" as used herein means that hemoglobin which aggregates into 14-stranded fibers at high intracellular concentrations and low partial pressure; such Hb S hemoglobin has an A to T transversion in the 6th codon of the human β-globin gene.

The term "positioned for expression" means that the DNA molecule is positioned adjacent to DNA sequences which direct transcription and translation of the sequence (i.e., facilitates the production of, e.g., anti-sickling hemoglobin).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated by reference. Unless mentioned otherwise, the techniques employed or contemplated herein are standard methodologies well known to one of ordinary skill in the art. The materials, methods, and examples are illustrative only, and not limiting.

The invention described herein provides a straightforward approach for the correction of a sickle cell anemia defect, and thus has important therapeutic value. Other features and advantages of the invention will be apparent from the following description of the preferred embodiments thereof, and from the claims.

DETAILED DESCRIPTION

The drawings are first described.

DRAWINGS

Figure 1A:
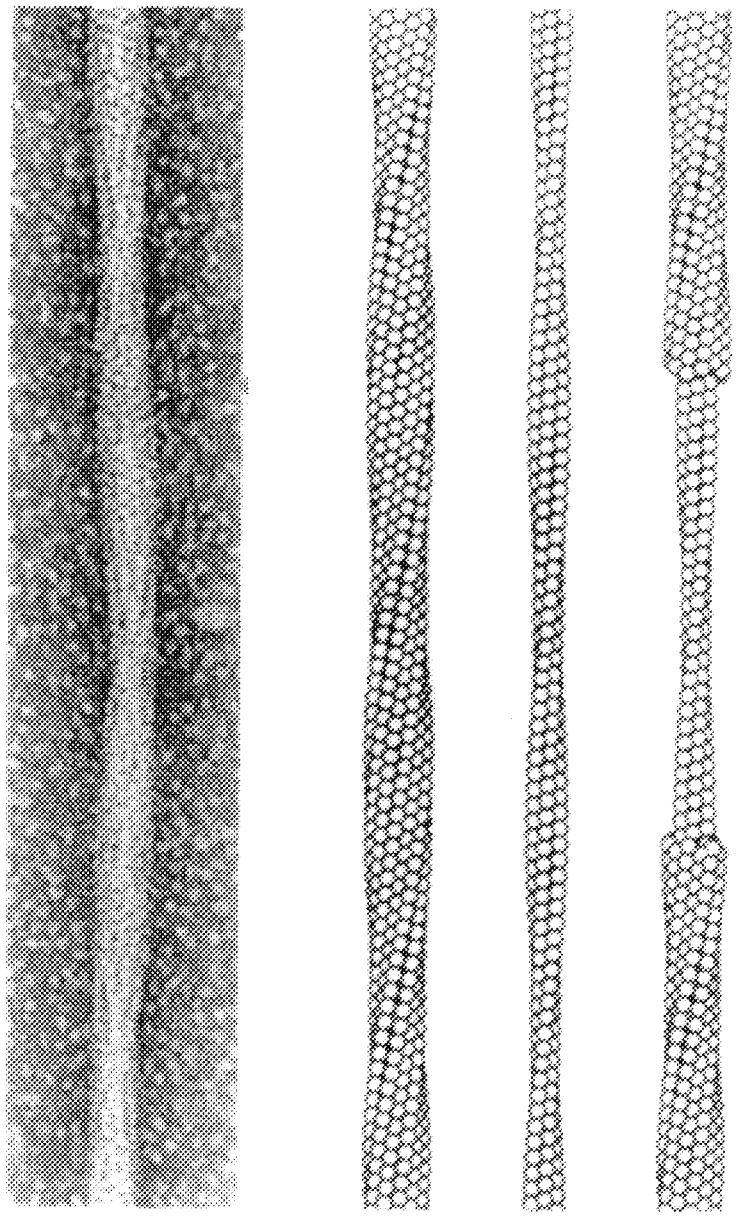

FIG. 1A is an electron micrograph of an Hb S fiber and a schematic representation of an Hb S fiber.

Figure 1B:
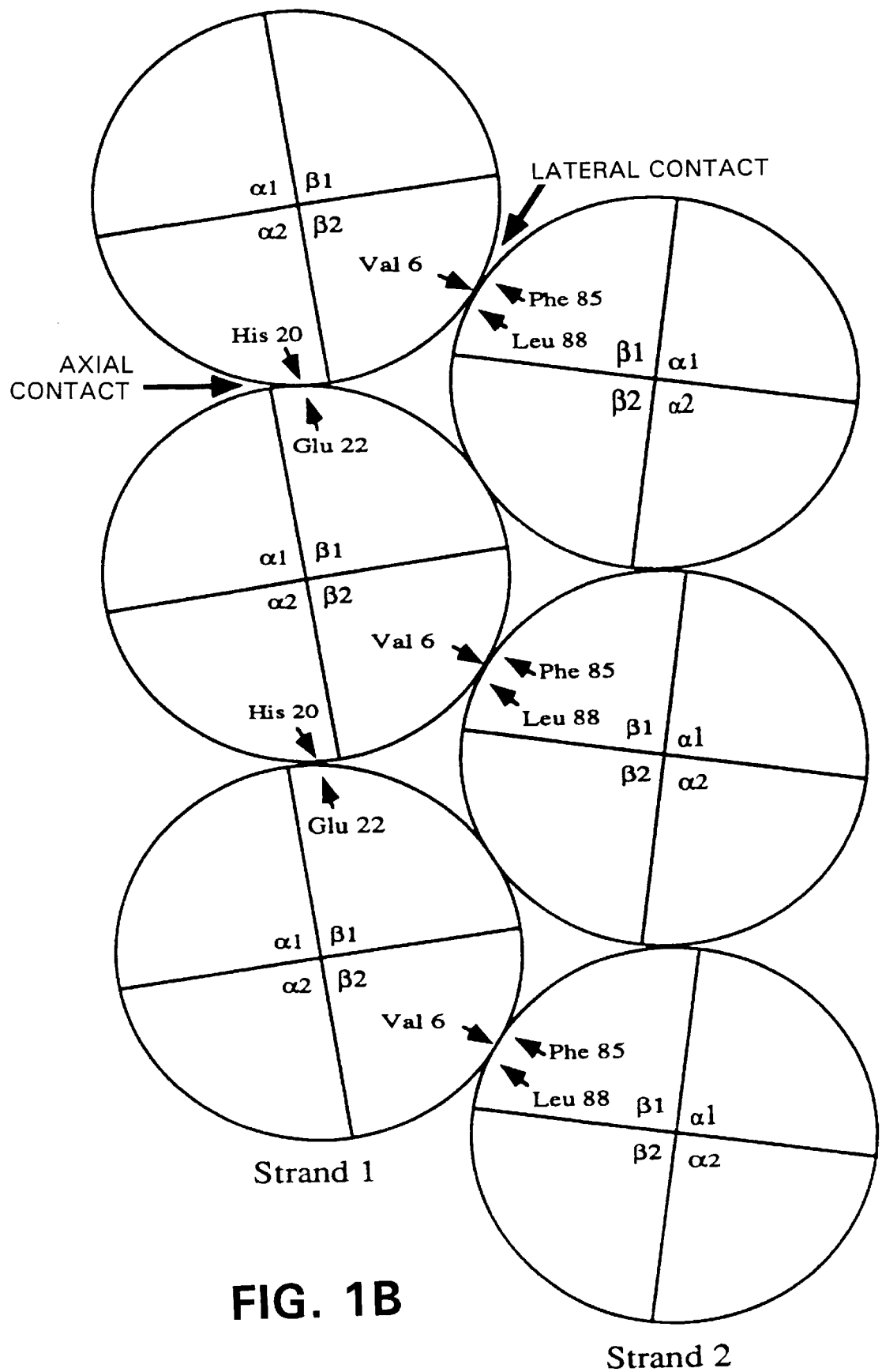

FIG. 1B is an illustration of the structure of the Hb S fiber. Each circle represents a Hb S tetramer. The fiber is composed of seven pairs of double stranded polymers; two double stranded polymers (4 strands) form the inner core and five double stranded polymers (10 strands) form the outer sheath. Two types of contacts occur between Hb S tetramers incorporated into fibers. Contacts along the long axis of the fiber are termed axial contacts, while contacts along the sides of tetramers are lateral contacts. The β6 valine plays a critical role in the lateral contact by interacting with the hydrophobic residues β85 phenylalanine and β88 leucine. An important axial contact is the interaction of the β22 glutamic acid with the imidazole group of the β20 histidine on an adjacent tetramer.

Figure 2:
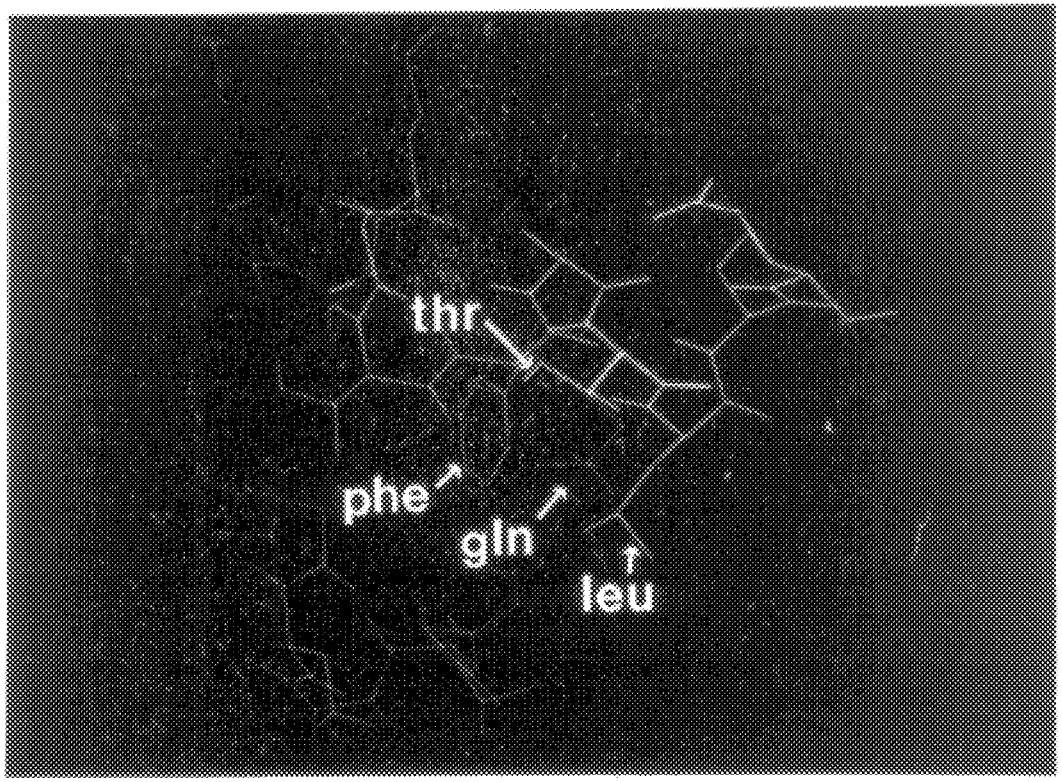

FIG. 2 is an illustration of a lateral contact in the double stranded Hb S polymer. This contact forms when the β6 valine of sickle hemoglobin interacts with a hydrophobic pocket on an adjacent tetramer. This hydrophobic pocket consists primarily of the residues β85 phenylalanine (phe) and β88 leucine (leu). These two residues are essential for correct positioning of the heme moiety and cannot be mutated. However, a threonine (thr) residue at position 87 can be replaced by a glutamine (gln), shown in red. The longer side chain of the glutamine prevents the β6 valine from interacting with the hydrophobic pocket.

Figure 3:
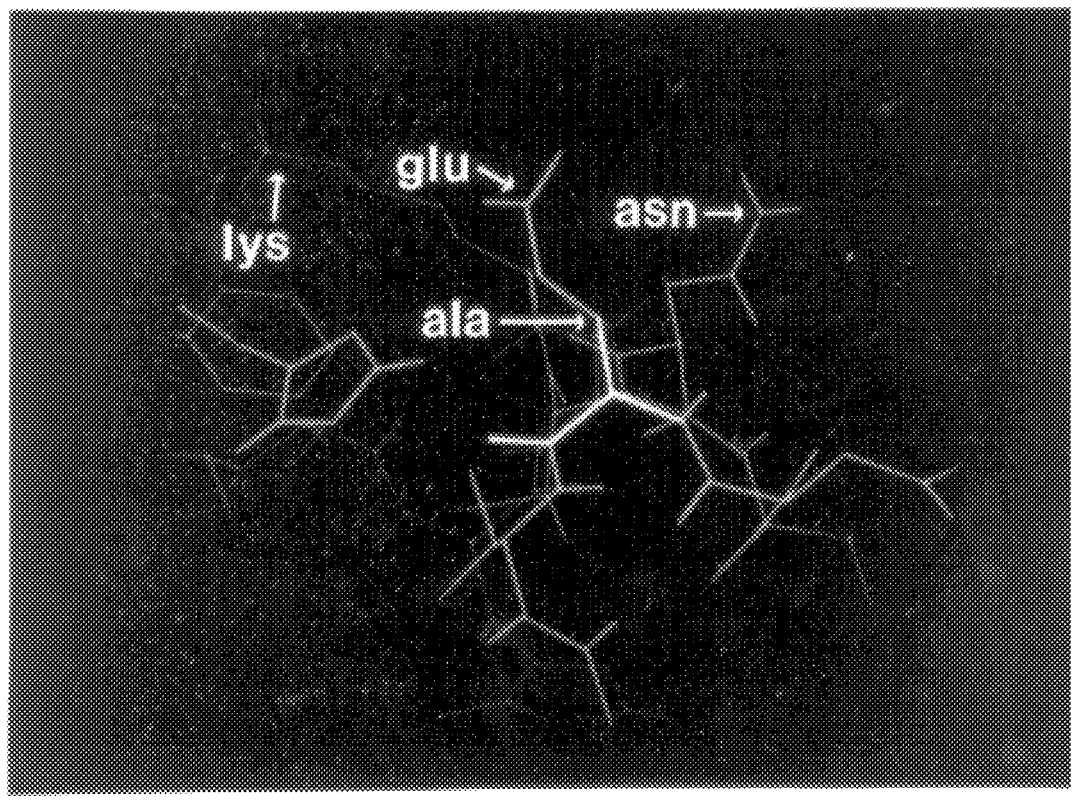

FIG. 3 is an illustration of an axial contact in the double stranded Hb S polymer. The side chains of the amino acids B17 lysine (lys), β19 asparagine (asn), and β22 glutamic acid (glu) project to form a surface which stabilizes the axial contact. In several of the anti-sickling hemoglobins, the β22 glutamic acid is replaced by an alanine residue (ala). This residue fails to interact with the positively-charged histidine from the neighboring tetramer and thus disrupts the axial contact. The new alanine residue is shown in light blue.

Figure 4:
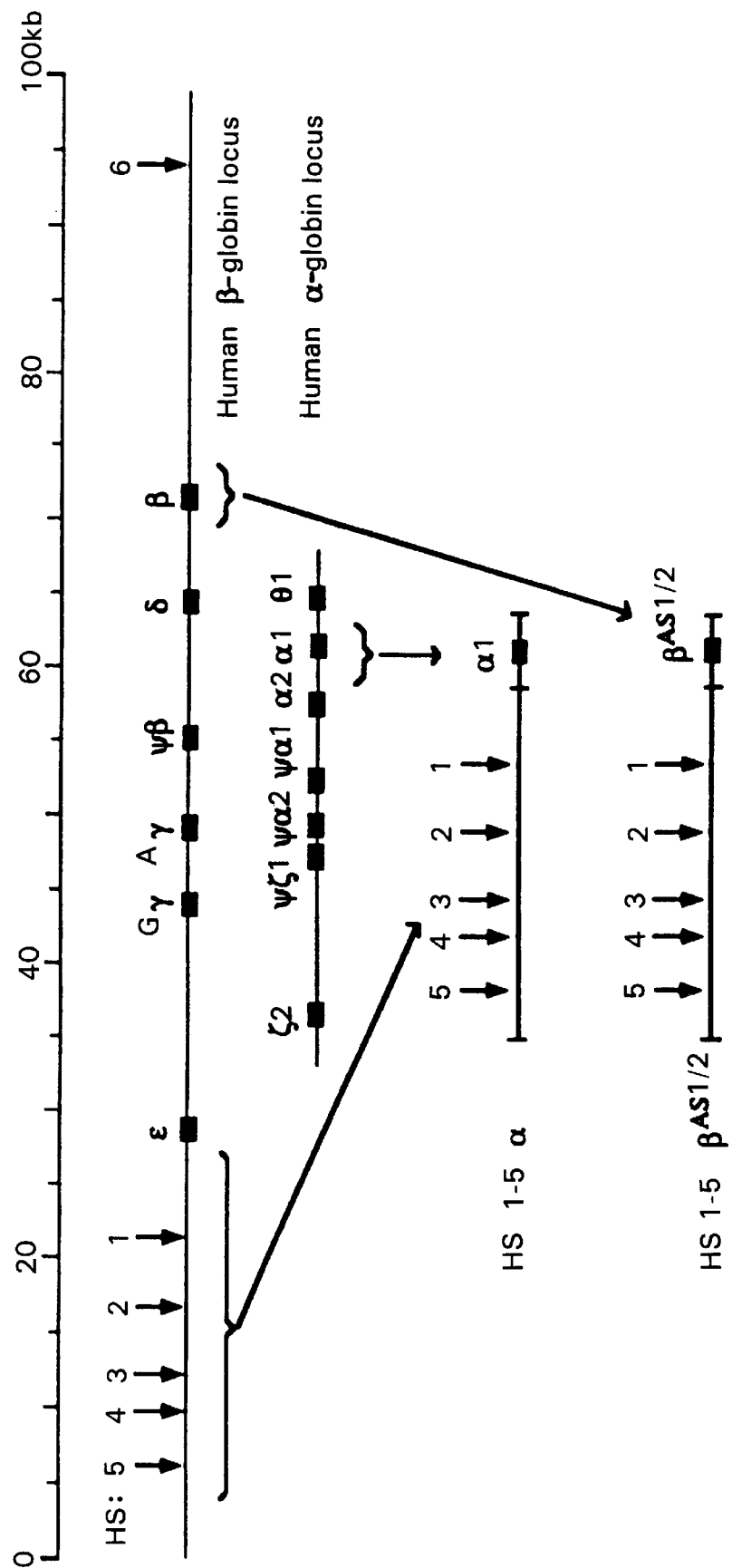

FIG. 4 is an illustration of 5' HS 1-5 α1 and HS 1-5 $\beta^{AS}$ constructs. One hundred kilobases of the human β-globin locus and 35 kilobases of the human α-globin locus are illustrated. Cosmids containing HS 1-5 α1 and HS 1-5 $\beta^{AS}$ were constructed by fusing either the α1 gene or a recombinant anti-sickling β-globin gene downstream of the β-globin locus control region (LCR). The 26 kb inserts were purified from vector sequences, mixed at a 1:1 molar ratio (final DNA concentration was 2 ng/μl), and co-injected into fertilized mouse eggs. Transgenic lines displaying high-level, balanced expression of the transgenes were established.

Figure 5A:
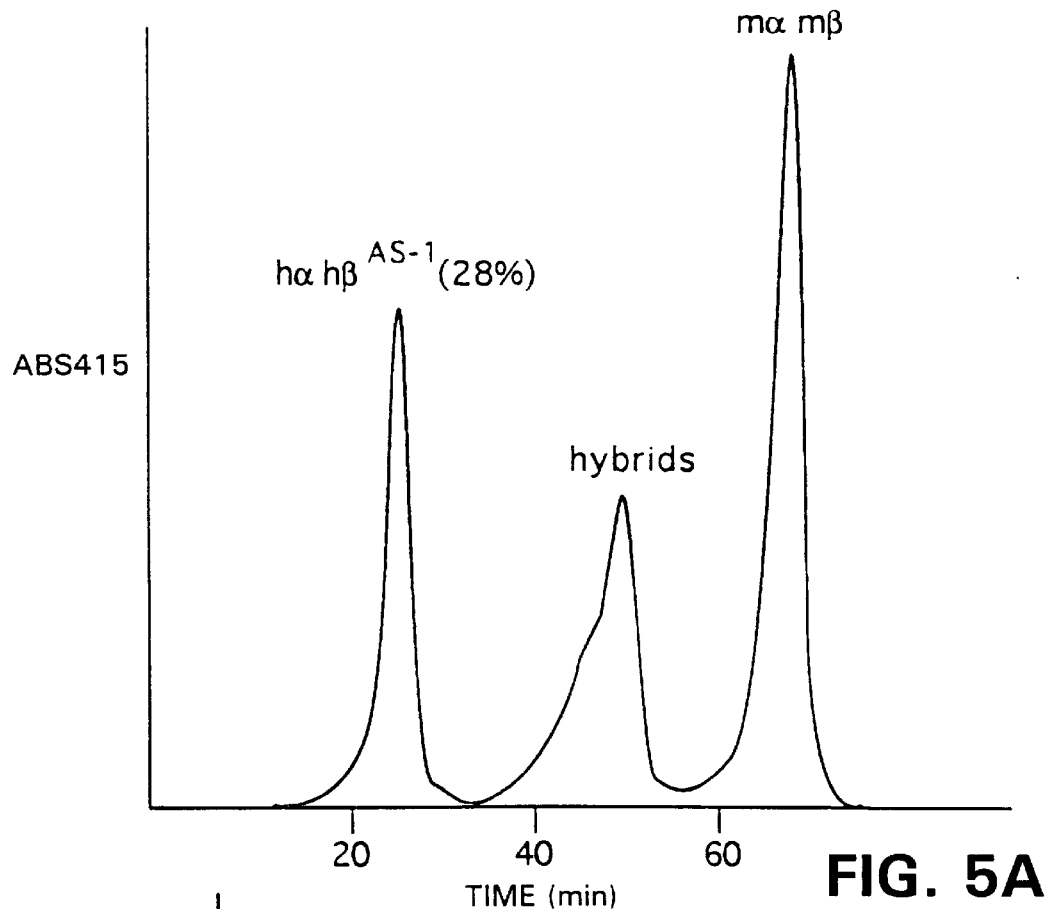
Figure 5B:
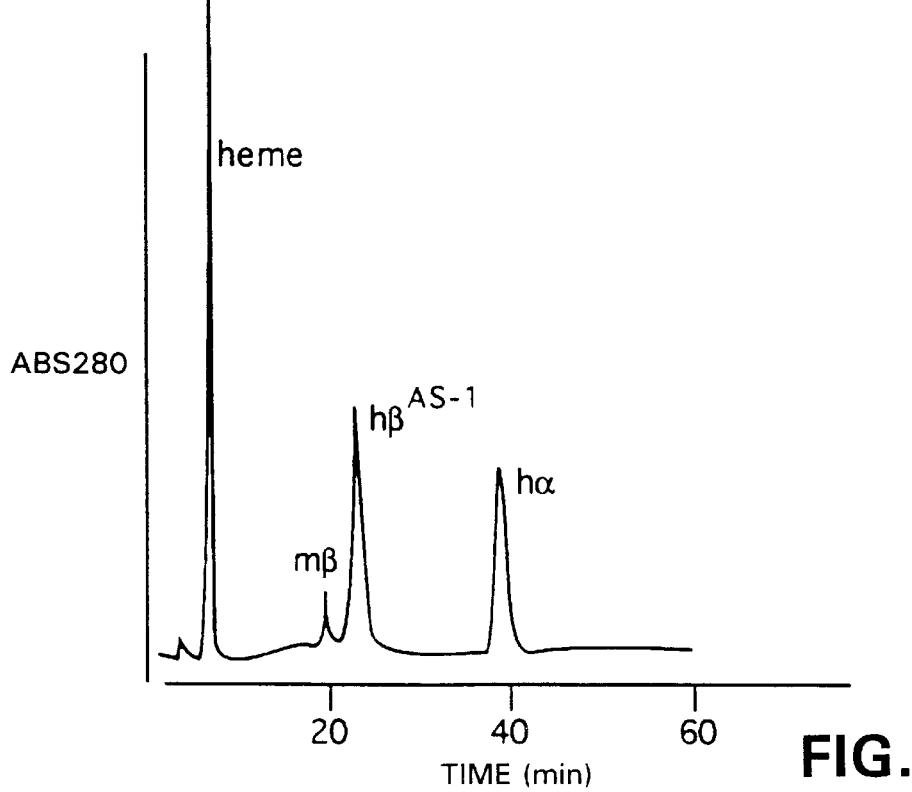
Figure 5C:
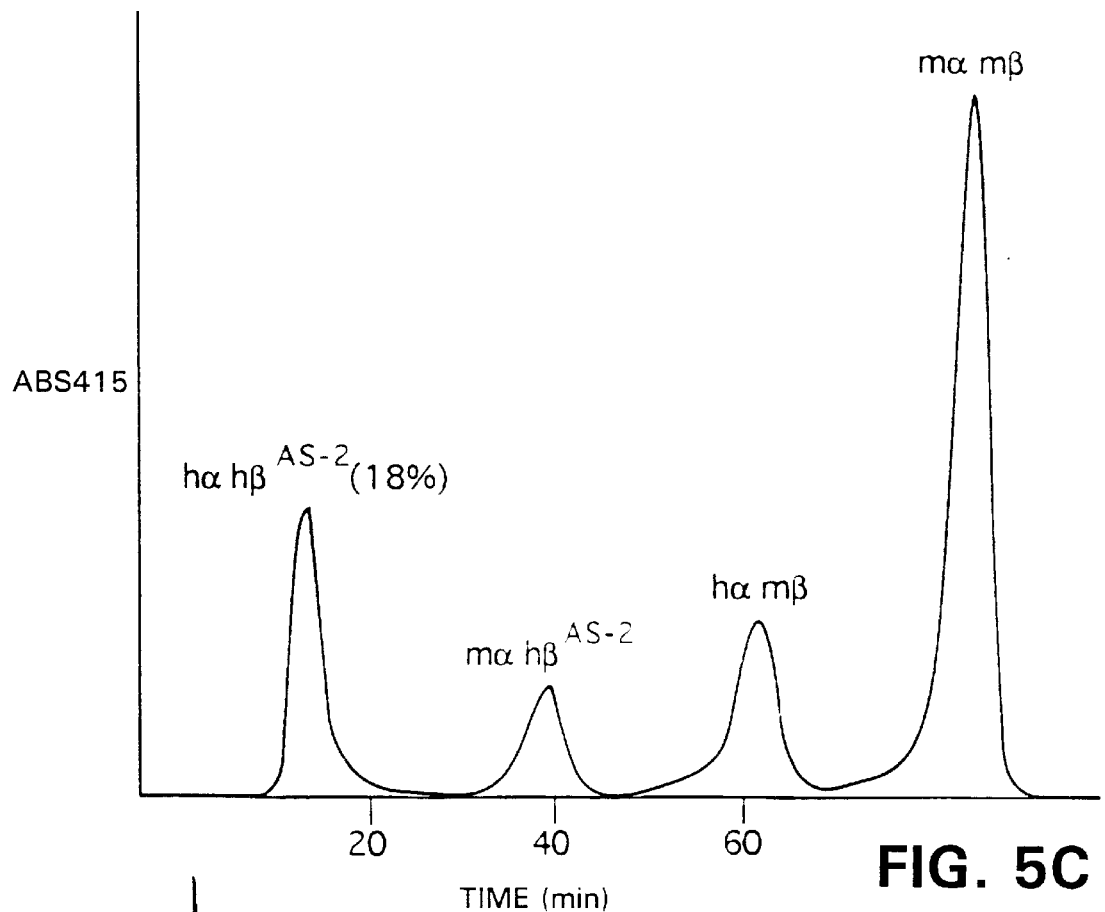
Figure 5D:
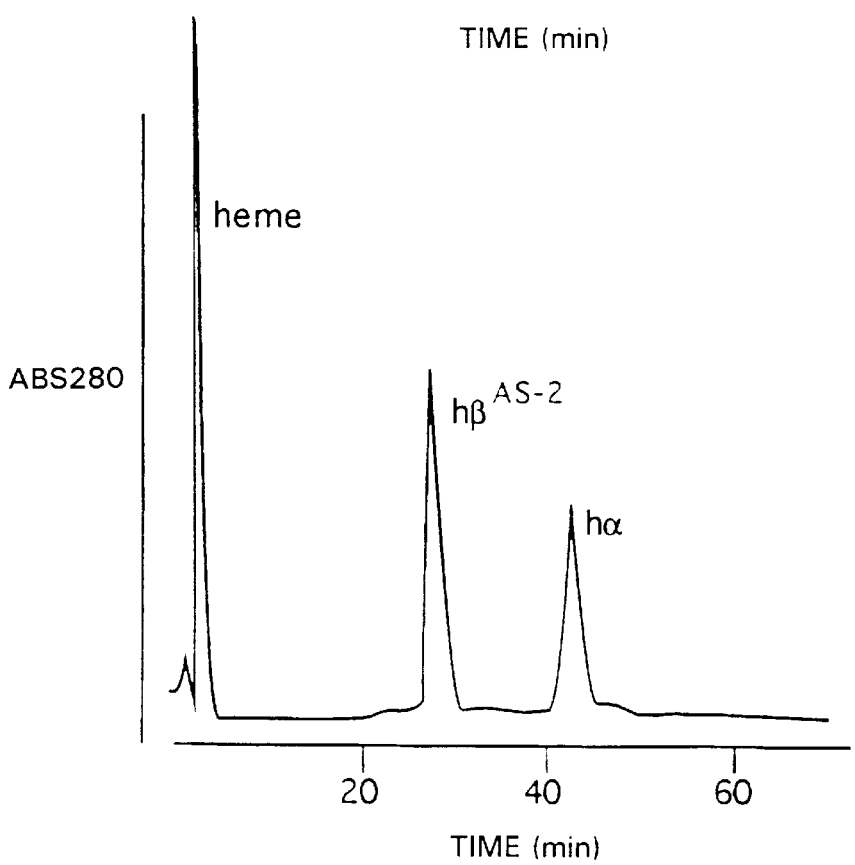

FIGS. 5A–5D are graphs of chromatographs of hemolysates and HPLC-purified anti-sickling hemoglobins. Fig. 5A is a graph of a chromatograph of hemolysate obtained from transgenic mice expressing Hb AS1. Hemoglobins were separated by non-denaturing HPLC. Twenty eight percent of the hemoglobin in erythrocytes of these animals is recombinant human $\alpha\beta^{AS1}$. FIG. 5B is a graph of denaturing HPLC analysis of $\alpha\beta^{AS1}$ purified from the hemolysate shown in FIG. 5A. Purification was performed by preparative isoelectric focusing (IEF). Approximately 10% of the β-globin chains were of murine origin. FIG. 5C is a graph of a chromatograph of hemolysate obtained from transgenic mice expressing Hb AS2. Hemoglobins were separated by non-denaturing HPLC. Eighteen percent of the hemoglobin in the erythrocytes of these animals is recombinant human $\alpha\beta^{AS2}$. FIG. 5D is a graph of denaturing HPLC analysis of $\alpha\beta^{AS2}$ purified from the hemolysate shown in FIG. 5C. Purification was performed by preparative IEF. This hemoglobin lacks any contaminating murine globins. Hemoglobins purified by preparative IEF were used in all subsequent experiments.

Figure 6A:
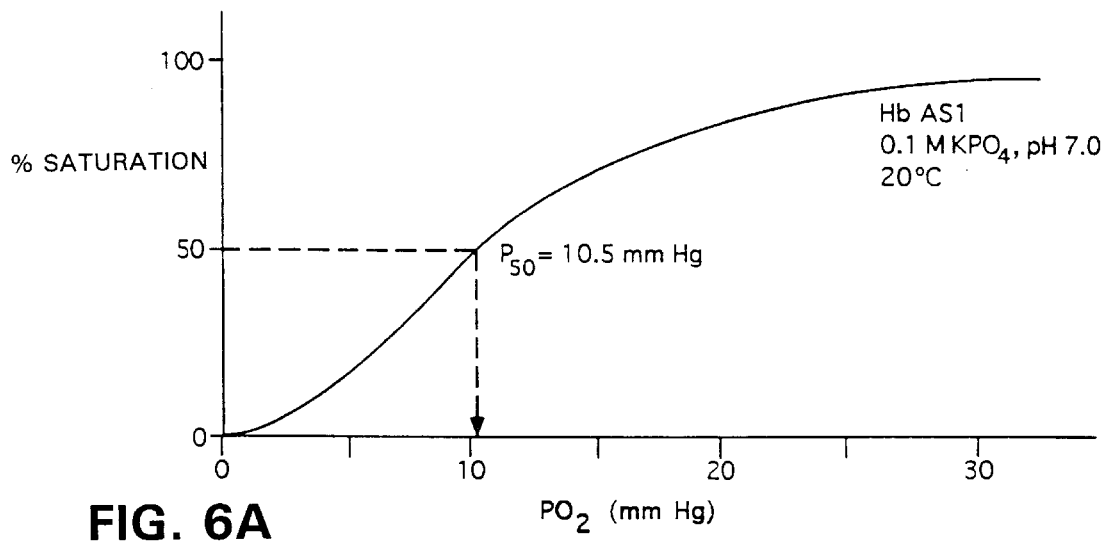
Figure 6B:
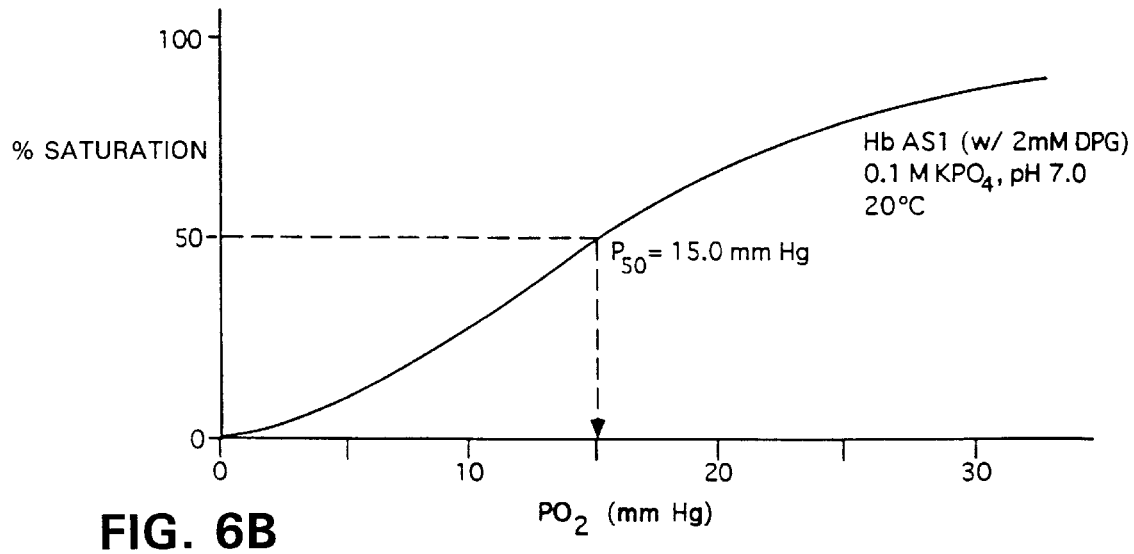
Figure 6C:
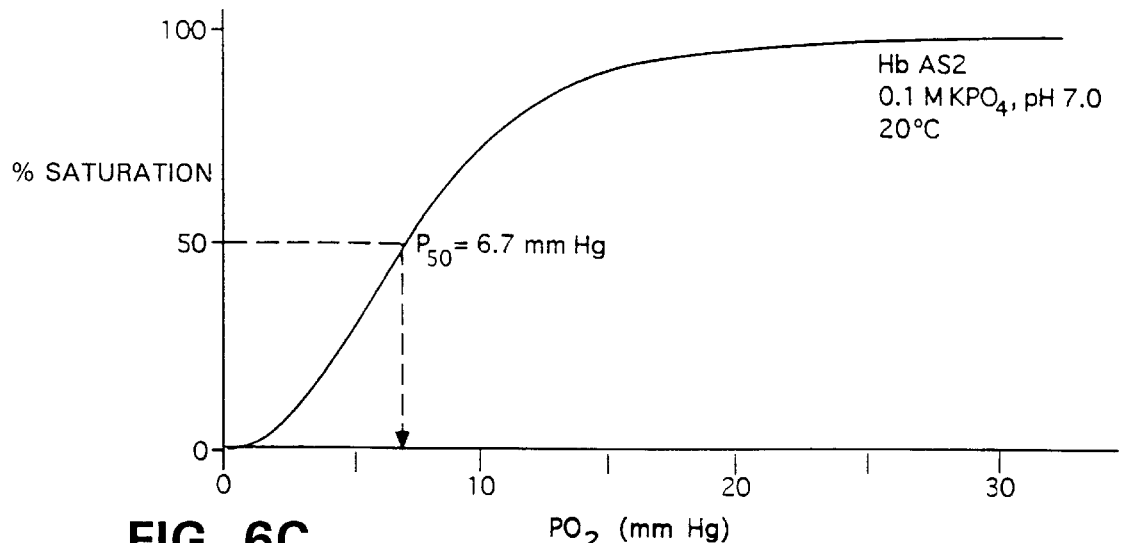
Figure 6D:
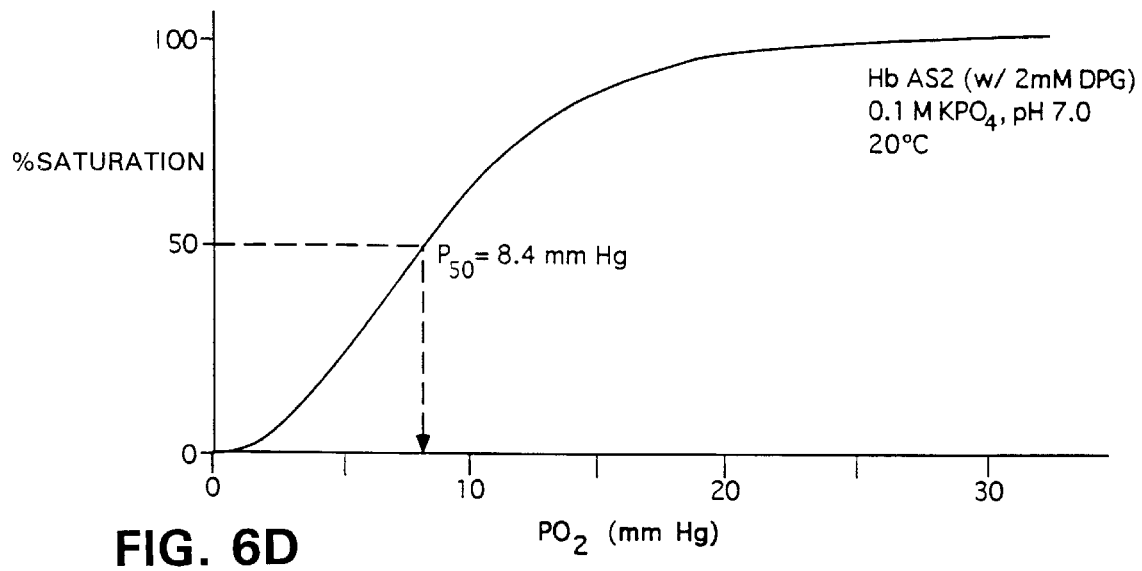

FIGS. 6A–6D are oxygen equilibrium curves (OECs) for purified human anti-sickling hemoglobins. FIG. 6A is an OEC curve for Hb AS1 at pH 7.0 in 0.1M potassium phosphate (KPO$_4$) buffer at 20° C. FIG. 6B is an OEC curve for Hb AS1 under the same conditions as those described in FIG. 6A, with the addition of 2 mM 2,3-diphosphoglycerate (DPG). FIG. 6C is an OEC curve for Hb AS2 at pH 7.0 in 0.1M KPO$_4$ buffer at 20° C. FIG. 6D is an OEC curve for Hb AS2 under the same conditions as those described in FIG. 6C with the addition of 2 mM 2,3-DPG.

Figure 7A:
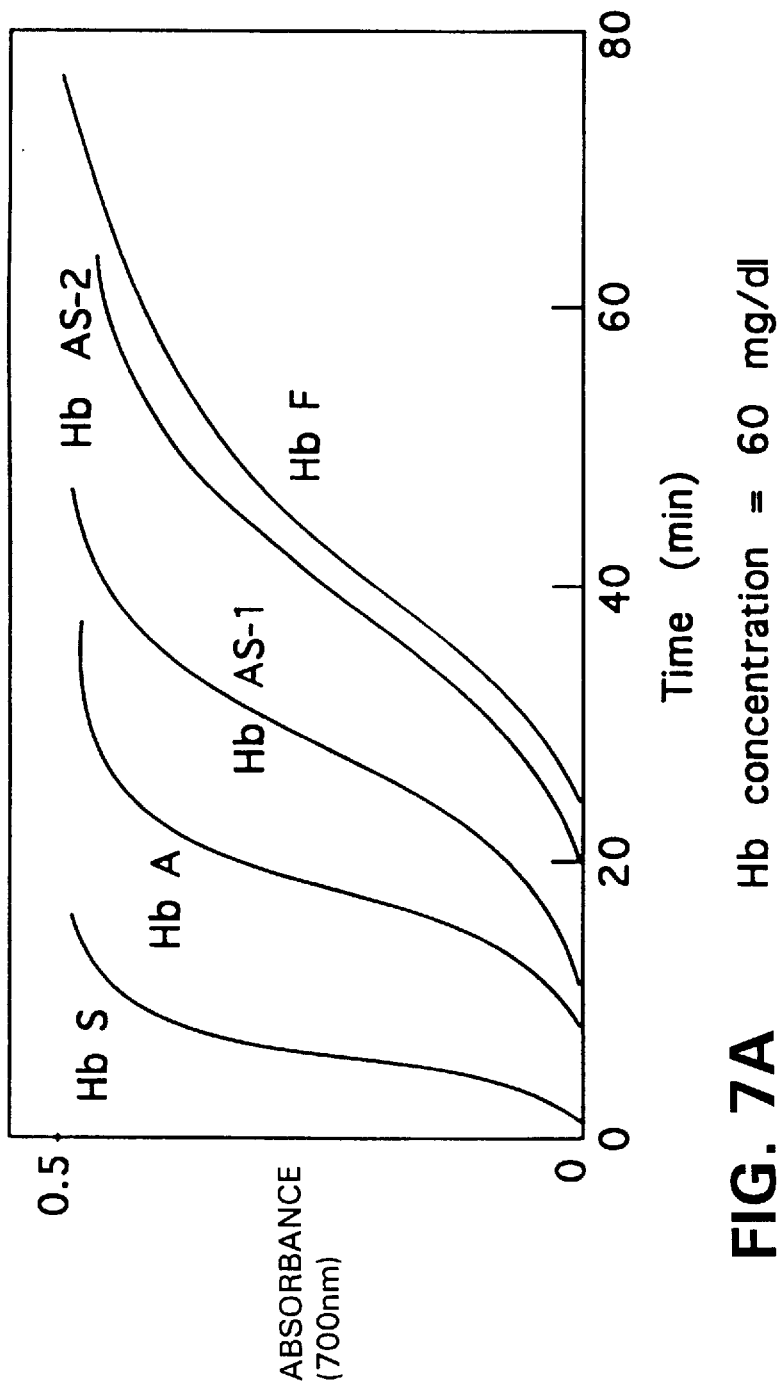
Figure 7B:
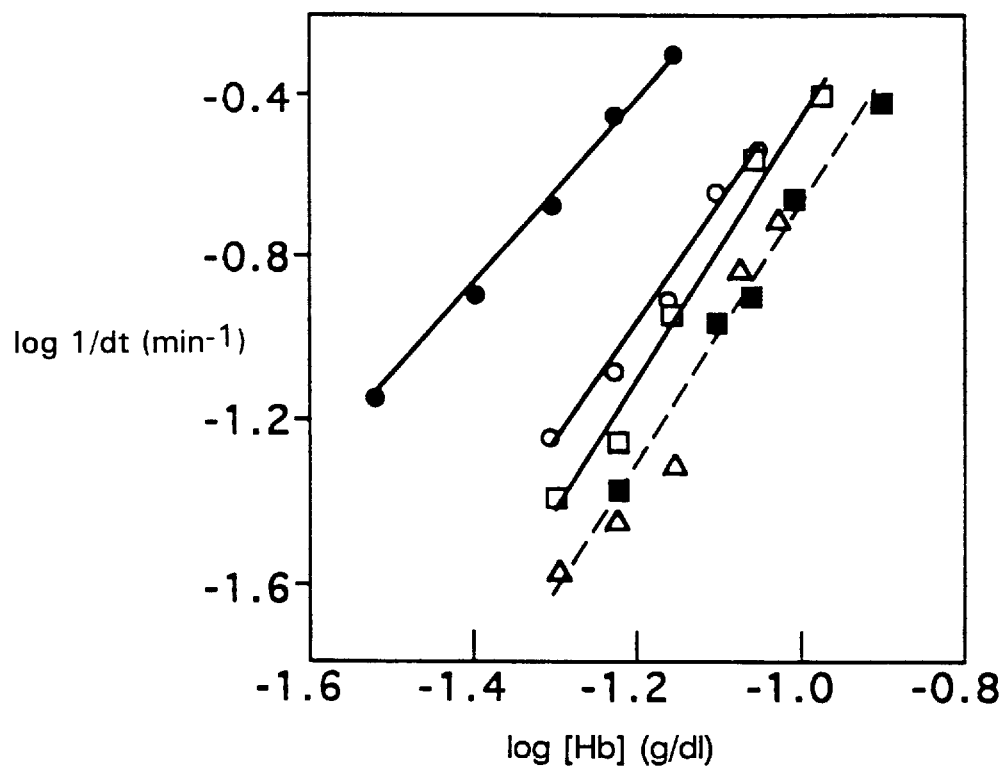

FIGS. 7A–7B are graphs showing polymerization delay times for deoxygenated mixtures of human hemoglobins. FIG. 7A shows delay times for hemoglobin mixtures containing 100% Hb S or 75% Hb S, together with 25% Hb A, Hb AS1, Hb AS2, or Hb F. Curves were determined at a hemoglobin concentration of 60 mg/dl using the temperature jump method (Adachi et al., J. Biol. Chem. 254:7765, 1979). The delay time is an indication of the ability of a hemoglobin to disrupt the polymerization of Hb S. The delay time of Hb AS1 is between that of Hb A and Hb F, while the delay time of Hb AS2 is similar to that of Hb F at this hemoglobin concentration. FIG. 7B shows delay time vs. hemoglobin concentration. The progression of the plots from left to right demonstrates the increased Hb concentrations which are required for polymerization to occur in the presence of the various non-S hemoglobins. The delay time plots for Hb AS2 and Hb F overlap, indicating that the anti-polymerization activities of Hb AS2 and Hb F are virtually identical.

Figure 8:
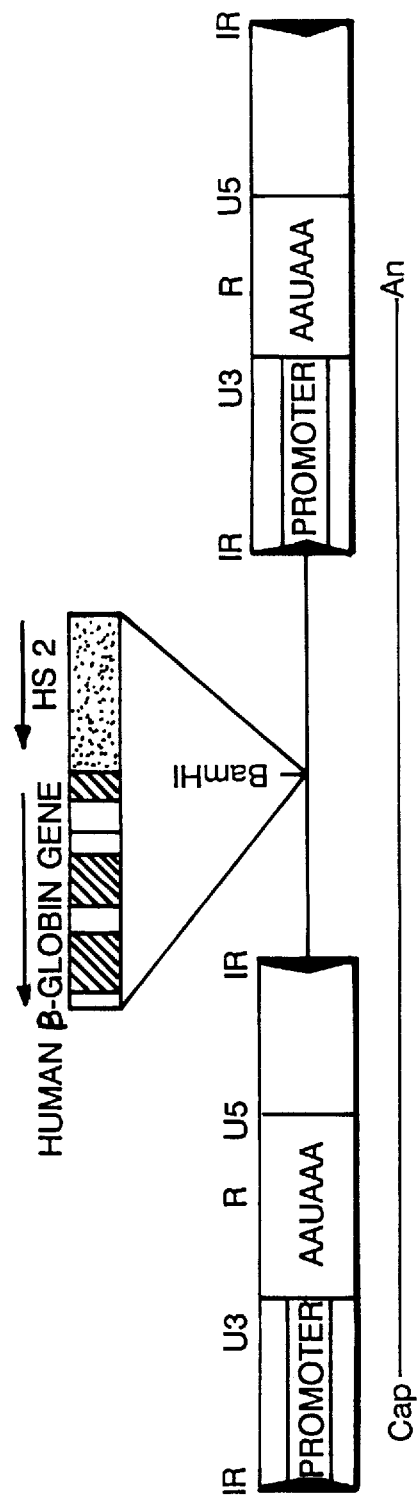

FIG. 8 is an illustration of a retroviral vector useful for the production of anti-sickling hemoglobin.

Anti-Sickling β-globin Genes Designed to Inhibit Hb S Polymerization

Recombinant hemoglobins of the invention which contain anti-sickling mutations can be used to inhibit Hb S polymerization, and thus facilitate therapies for sickle cell anemia. In particular, the glutamic acid to valine change at the 6th position of the $\beta^S$ polypeptide creates a non-polar surface that readily interacts with a natural hydrophobic pocket in the β chain of a second tetramer. This natural pocket is formed primarily by a phenylalanine (phe) at position 85 and a leucine (leu) at position 88. This interaction leads to the formation of the complex 14-stranded fibers described above, and illustrated in FIGS. 1A–1B (Bunn et al., *Hemoglobin: Molecular, Genetic, and Clinical Aspects*, 1986, W. B. Saunders, Philadelphia).

The structure of the fiber that forms in sickle erythrocytes was derived from X-ray diffraction studies of Hb S crystals (Edelstein, J. Mol. Biol. 150:557, 1981). Hb S tetramers are composed of two α-globin subunits ($\alpha_2$) and two $\beta^S$-globin subunits ($\beta^S_2$), and form characteristic double stranded fibers. Interactions along the long axis of the fiber are termed axial contacts, while interactions along the sides of tetramers are lateral contacts (FIG. 1B; Bunn et al., *Hemoglobin: Molecular, Genetic, and Clinical Aspects*. (W. B. Saunders, Philadelphia, 1986)). The β6 valine plays a critical role in the lateral contact by interacting with the hydrophobic residues β85 phenylalanine and β88 leucine (FIG. 2). Accordingly, to interfere with detrimental Hb S polymerization, this interaction and, thus, hydrophobic pocket formation should be disrupted. Because Hb A ($\alpha_2\beta_2$) has these same hydrophobic residues and is readily incorporated into sickle fibers, it cannot be used for this purpose. Moreover, although disruption of this pocket represents the best approach for inhibiting Hb S polymerization, certain strategies have detrimental side effects. For example, although amino acid substitutions at β85 phe and β88 leu would interfere with pocket formation, these amino acids are also important for correct positioning of the heme moiety, and cannot be mutated without severely altering oxygen affinity (Dickerson et al., *Hemoglobin: Structure, Function, Evolution, and Pathology*. (Benjamin/Cummings, Menlo Park, Calif., 1983)).

A better approach for inhibiting Hb S polymerization is depicted in FIG. 2 which shows a computer model of a β87 threonine (thr) to glutamine (gln) substitution that disrupts the hydrophobic pocket, without inhibiting β-globin function (Perutz et al., Nature 219:902–909, 1968; Computer graphics generated using an Evans and Sutherland PS300 system running the package FRODO (Jones, Meth. Enz. 115:157, 1985)). The long side chain of glutamine prevents the β6 Val from interacting with the hydrophobic pocket. Human γ- and δ-globin polypeptides both have such a glutamine at position 87, and both Hb F ($\alpha_2\gamma_2$) and Hb A2 ($\alpha_2\delta_2$) have potent anti-sickling activity (Nagel et al., Proc. Natl. Acad. Sci., USA 76(2):670–672, 1979). Another naturally occurring human hemoglobin, designated Hb D Ibadan, also has anti-sickling activity (Watson-Williams et al., Nature 205:1273, 1965). This hemoglobin has a lysine at position 87 and its long side chain also projects across the hydrophobic pocket and inhibits interactions with the β6 Val.

Preferably, to produce a recombinant anti-sickling hemoglobin, the mutations described above (which interfere with a major lateral contact) are combined with a second mutation which interferes with an axial contact. One such axial contact-disrupting mutation is shown in FIG. 3. The side chains of the amino acids lysine-17 (lys), asparagine-19 (asn), and glutamic acid-22 (glu) project to form a surface which stabilizes the axial contact with another sickle hemoglobin tetramer (Dickerson et al., *Hemoglobin: Structure, Function, Evolution, and Pathology*. (Benjamin/Cummings, Menlo Park, Calif., 1983)). Although mutations at residues 17 or 19 are detrimental, amino acid 22 can be mutated from glutamic acid to alanine (ala) without an alteration in hemoglobin function (Bowman et al., Biochemical and Biophysical Research Communications 26(4):466–470, 1967; Bunn et al., *Hemoglobin: Molecular, Genetic, and Clinical Aspects*. (W. B. Saunders, Philadelphia, 1986)). The negative charge of the glutamic acid side chain at this position plays a key role in stabilizing the axial contact because it interacts with the positively charged imidazole group of a histidine at position 20 in the α chain of the neighboring tetramer. The shorter nonpolar alanine side chain fails to stabilize this interaction, thus disrupting the axial contacts between sickle hemoglobin tetramers. The substituted alanine residue is shown in light blue in FIG. 3. Hb AS2 contains a glutamine at position 87 together with an alanine at position 22. Hb AS1 has the same β22 alanine and asparagine at β80 is replaced by lysine. This β80 lysine significantly inhibits sickling when present as a single site mutation in Hb A (Nagel et al., Nature 283:832, 1980). The following 27-mer oligos were used for mutagenesis at the indicated amino acids in β-globin: β22, GTGAACGTG-GATGCCGTTGGTGGTGAG (SEQ ID NO: 1); β80, GCT-CACCTGGACAAGCTCAAGGGCACC (SEQ ID NO: 2); β87, GGCACCTTTGCCCAGCTGAGTGAGCTG (SEQ ID NO: 3).

Another anti-sickling mutation in the human β-globin gene useful in the invention is the Hb G Szuhu mutation, a β80 asn to lys mutation which has significant anti-sickling activity (Nagel et al., Proc. Natl. Acad. Sci. USA 76(2):670–672, 1979), but which does not impair hemoglobin function (Kaufman et al., Human Heredity 25:60–68, 1975).

This mutation is preferably combined with the β22 glu to ala mutation described above.

Alternatively, an α-globin mutation may be utilized to inhibit Hb S polymerization. One example of such an α-globin mutation is provided by the hemoglobin designated Hb Montgomery (Brimhall et al., Biochim. Biophys. Acta. 379(1):28–32, 1975), which contains an α48 leucine to arginine mutation. The 54 year old patient from which this mutation was isolated was homozygous for $\beta^S$, but had no history of painful sickle cell crises, jaundice, leg ulcers, or stroke, and was only mildly anemic (Prchal et al., Am. J. Med. 86(2):232–236, 1989).

Anti-sickling hemoglobin AS3 combines the mutations at β22 and β87, which are present in anti-sickling hemoglobin AS2, with an additional mutation which lowers the oxygen affinity of the recombinant hemoglobin. The goal is to produce an anti-sickling hemoglobin which delivers oxygen to tissues prior to sickle hemoglobin (Hb S). We have termed this concept "preferential deoxygenation." If the anti-sickling hemoglobin delivers oxygen preferentially, Hb S will remain oxygenated and, therefore, will not polymerize.

The mutation which was selected to lower the oxygen affinity of the anti-sickling hemoglobin is a change from asparagine to lysine at position 108 of the β-globin chain. This is the mutation which is present in the naturally-occurring Hb Presbyterian (Moo-Penn et al., FEBS Letters 92:53–56, 1978). Hb AS3 has the following three mutations: (1) β22 glutamic acid to alanine, (2) β87 threonine to glutamine, and (3) β108 asparagine to lysine.

Two additional anti-sickling hemoglobins, AS4 and AS5, have been made which combine the mutations present in Hb AS2 at β22 and β87, with additional mutations which cause the β-globin subunit to become more negatively charged. In red blood cells, surface charge is a key determinant of the ability of α-globin and β-globin monomers to associate with each other to form dimers (Bunn, Blood 69:1–6, 1987). The alpha subunit is somewhat positively-charged, while the beta subunit is somewhat negatively-charged. By increasing the negative charge on the β-globin subunit, it is possible to increase its affinity for the α-globin subunit. Introduction of an additional negative charge in the anti-sickling hemoglobin will provide $\beta^{AS}$ polypeptides with a competitive advantage for interacting with α-globin polypeptides. Consequently, $\alpha_2\beta^{AS}_2$ tetramers will form more efficiently than $\alpha_2\beta^S_2$ tetramers.

Anti-sickling hemoglobins Hbs AS4 and AS5 combine the mutations present in AS2 with a mutation which increases the negative charge on the β-globin subunit. One mutation which increases the negative charge on the β-globin subunit but which does not affect the normal functioning of the hemoglobin molecule is a change from lysine to glutamic acid at position 95. This mutation occurs naturally and is known as Hb N-Baltimore. The resulting change in charge is −2, since a positively-charged lysine is replaced by a negatively-charged glutamic acid. This change in charge also allows Hb AS4 and Hb S to be distinguished by isoelectric focusing. Hb AS4 has the following three mutations: (1) β22 glutamic acid to alanine, (2) β87 threonine to glutamine, and (3) β95 lysine to glutamic acid.

An additional mutation which occurs naturally and which is known to increase the ability of the β-globin subunit to compete for the α-globin subunit is known as Hb J-Baltimore. This mutation consists of a change from glycine to aspartic acid at position 16 of the β-globin subunit. While this mutation adds only one additional negative charge to the β-globin chain (compared to the two negative charges added by the N-Baltimore mutation described above), the location of the negative charge is significant. In fact, Hb J-Baltimore competes even more effectively than Hb N-Baltimore for the α-globin subunit. Hb AS5 has the following three mutations: (1) β16 glycine to aspartic acid, (2) β22 glutamic acid to alanine, and (3) β87 threonine to glutamine.

The invention includes anti-sickling hemoglobins that contain any combinations of the individual mutations described above. For example, the β108, β95, and β16 mutations may occur either alone, in combination with the β22 mutation, or in combination with the β22 mutation and either the β80 or either of the above-described β87 mutations.

Mutagenesis of Human α- and β-globin Genes

Mutations may be introduced into the normal human α-and β-globin genes by site-directed mutagenesis. For example, a 3.8 kb BglII-EcoRI fragment containing the human α-globin gene or a 4.1 kb HpaI-XbaI fragment containing the human β-globin gene may be cloned into the pSELECT plasmid (Lewis et al., Nucl. Acids. Res. 18:3439–3443, 1990; pSELECT is available from the American Type Culture Collection, Rockville, Md., ATCC# 68196) using standard methods (see e.g., Maniatis et al., 1989, *Molecular Cloning; A Laboratory Manual,* Cold Spring Harbor Laboratory, Cold Spring Harbor, N.Y.). Oligonucleotide mutagenesis is performed, e.g., as described by Lewis et al. (Nucl. Acids. Res. 18:3439–3443, 1990). In this procedure, an oligonucleotide which corrects a mutation in the ampicillin resistance gene in the pSELECT plasmid is used simultaneously with one or more oligonucleotides designed to create mutations in the globin gene insert.

Briefly, *E. coli* (JM109; ATCC# 53323) containing the pSELECT plasmid with globin gene inserts are infected with helper phage (M13K07). After growing the culture overnight (about 12–16 hours), phage obtained from the supernatant are extracted with phenol:chloroform, and single-stranded DNA is isolated by standard methods. Oligonucleotides containing each of the mutations are annealed to single-stranded DNA together with the wild-type ampicillin oligonucleotide, and these primers are extended with Klenow for about 90 minutes at 37° C. Double-stranded DNA is transformed into *E. coli* (BMH 71-18 muts), and the culture is grown overnight in L-broth containing 75 µg/ml ampicillin. DNA obtained from rapid lysis preparations of these cultures is transfected into *E. coli* (JM109), and colonies are selected on ampicillin plates (75 µg/ml). Double-stranded DNA obtained from rapid lysis preparations of these colonies is sequenced (Sanger et al., Proc. Natl. Acad. Sci. USA 74:5463–5467, 1977) using oligonucleotide primers located upstream of the mutagenic oligonucleotides. Mutants are clearly identified by comparison to wild-type sequence.

Construction of Cosmid Clones

The DNA constructs used to produce transgenic animals that synthesize high levels of anti-sickling hemoglobins are illustrated in FIG. 4. Constructs used for microinjection are as described by Behringer et al. (Science 245:971, 1989), except that the gene for sickle hemoglobin is replaced with genes encoding anti-sickling hemoglobins. Mutations are introduced into the human β-globin gene by site-specific mutagenesis, as described above, and the mutant sequences are inserted downstream of a 22 kb DNA fragment containing the DNAse hypersensitive sites 1–5 (5' HS 1–5) of the β-globin LCR (Lewis et al., Nucleic Acids Res. 18:3439, 1990), as described in further detail below.

In order to construct cosmid clones containing mutant α- and β-globin genes, the mutant genes are excised from pSELECT plasmids and subcloned into "right arm" plasmids containing a Cos site. Specifically, a 1.2 kb NcoI-XbaI fragment from the α-globin pSELECT plasmids and a 1.4 kb ClaI-BamHI fragment from the β-globin pSELECT plasmids are inserted into right arm plasmids in place of the corresponding α- and β-globin gene wild-type fragments. The α-globin right arm plasmids are digested with ClaI and MluI, and 4.8 kb fragments containing mutant α-globin genes which are linked to Cos sites are purified by agarose gel electrophoresis. The β-globin right arm plasmids are digested with ClaI and HindIII, and 6.5 kb fragments containing mutant β-globin genes which are linked to Cos sites are purified similarly. Cosmids containing these fragments are constructed in four way ligations (Ryan et al., Genes Dev. 3:314–323, 1989). The left arms are 9.0 kb MluI-SalI fragments obtained from the cosmid vector pCV001 (Lau et al., Proc. Natl. Acad. Sci. U.S.A. 80:5225–5229, 1983). This fragment contains a Cos site, an ampicillin resistance gene, a ColE1 origin and the SVneo gene. The two internal fragments are a 10.7 kb SalI-KpnI fragment containing DNase I super-hypersensitive (HS) sites V, IV and III, and a 10.9 kb KpnI-ClaI fragment containing HS II and I. The four fragments are ligated together in a 2:1:1:2 molar ratio of vector arms to inserts and packaged (Packagene; Promega, Madison, Wis.). *E. coli* ED8767 is infected with the packaged cosmids and is plated onto ampicillin plates. Large scale cultures of ampicillin resistant colonies are grown, and cosmids are prepared by standard procedures.

Transgenic animal assays—Characterization of anti-sickling hemoglobins

The effects of anti-sickling hemoglobin can be analyzed using transgenic animals. Cosmid DNA is prepared by standard procedures. HS I-V α and HS I-V β cosmids containing the mutations described above are either injected directly into fertilized mouse eggs, or the constructs are digested with SalI and insert DNA is separated from plasmid DNA by agarose gel electrophoresis prior to injection. The injected eggs and transferred to pseudopregnant foster mothers (Brinster et al., Proc. Natl. Acad. Sci. USA 82:4438–4442, 1985), and transgenic progeny are identified by Southern blot hybridization of tail DNA. Similarly, large animal eggs can be injected with the same constructs and transferred to foster mothers as described by Pursel et al. (Science 244:1281–1288, 1989). Typically, human α- and β-globin genes are cloned into expression vectors designed to direct high levels of α- and β-globin synthesis in erythroid cells of transgenic animals. These constructs are co-injected into fertilized mouse eggs and expression is analyzed in transgenic animals that develop.

Blood collected from transgenic animals is washed with saline, and hemolysates prepared as described by Ryan et al. (Science 245:971–973, 1990). Hemoglobin is analyzed on isoelectric focusing (IEF) gels (Ryan et al., Science 245:971–973, 1990) to demonstrate that a complete human hemoglobin is formed in adult erythrocytes, and to identify transgenic animals which synthesize high levels of human hemoglobin (Ryan et al., Science 247:566, 1990; Behringer et al., Science 245:971, 1989). Human hemoglobin bands are excised from IEF gels and analyzed on urea cellulose acetate strips to demonstrate that the human hemoglobin band is composed of human α- and β-globin polypeptides. It is noted that if human hemoglobin is difficult to separate from endogenous hemoglobins, mutations that increase or decrease the isoelectric point (pI) of human hemoglobin can be introduced into the α- and β-globin genes. Increases in pI are accomplished by introducing basic (positively charged) amino acids into the protein, while decreases in pI are accomplished by introducing acidic (negatively charged) amino acids. These charged amino acids are introduced at positions which do not disturb the structure or function of the protein. Oxygen equilibrium curves (OECs) of human hemoglobin purified from the transgenic mice are determined as described by Ryan et al. (Science 247:566–568, 1990).

The anti-sickling properties of the AS hemoglobins (purified from erythrocytes of the above-described transgenic animals) can be quantitated by in vitro solubility assays as described, e.g., by Benesch et al. (J. Biol. Chem. 254:8169, 1979). Briefly, the anti-sickling hemoglobin is mixed with Hb S. The solution is cooled to 0° C., deoxygenated, and then incubated at 30° C. for 2 to 3 hours. Insoluble polymers are pelleted by ultracentrifugation, and the concentration of hemoglobin in the supernatant is determined spectrophotometrically. The solubility of mutant hemoglobin/Hb S mixtures is compared with Hb A/Hb S and Hb F/Hb S solutions.

Retroviral Vectors Designed To Correct the Sickle Defect

The anti-sickling hemoglobin genes described herein may be used to correct a sickling defect by gene therapy. Such techniques are first tested in an animal model, for example, mice, but similar techniques may be used to treat other mammals, including humans. A description of a retroviral vector useful for transferring anti-sickling hemoglobin genes to a mammal now follows.

As a first step toward gene therapy, the anti-sickling β-globin genes described above are preferably inserted into a retroviral vector such as that illustrated in FIG. 4. This vector is of a small size to optimize the viral titers obtained. To construct such a small vector, a minimum HS 2 region (Caterina et. al., Proc. Natl. Acad. Sci. USA 88:1626–1630, 1991) of the globin LCR is inserted upstream of the β-globin gene; this 1.1 kb KpnI-XbaI fragment containing HS 2 retains sequences required for both enhancer and domain opening activity, facilitating high level expression of downstream β-globin genes with minimum size. In addition, the vectors include mini-globin genes which contain only 200 bp of 5' flanking sequence and 150 bp of 3' flanking sequence, and only 100 bp of IVS 2. The mini-globin genes, although small, contain all of the sequences necessary for high level expression, including the TATA (−35), CCAAT (−70) and CACCC (−100) boxes (Antoniou et al., Genes Dev. 4:1007–1013, 1990; Antoniou et al., Genes Dev. 4:1007–1013, 1990). They also contain all sequences required for correct splicing of the β-globin second intron, including the splice donor, splice acceptor, and branch point sequences.

Another feature of these constructs is the use of a deleted SV-Neo region (SN) of LXSN (Miller et al., Biotechniques 7(9):980–990, 1989); this deletion removes 1.5 kb of DNA and significantly reduces the size of the construct. Although these viruses cannot be easily titered by conventional means, viral titers can be estimated by Southern blot hybridization of NIH 3T3 cells that are infected with supernatants from packaging cells lines. Briefly, to carry out such an assay, the constructs described above are co-transfected with an SV-Neo plasmid into an ecotropic and/or amphotropic packaging cell line (for example, E86 and PA317) (Markowitz et al., Virology 167(2):400–406, 1988; Markowitz et al., J. Virol. 62(4):1120–1124, 1988; Miller et al., Mol. Cell Biol. 6:2895–2902, 1986), and colonies of G418 resistant cells are isolated. Undiluted and serially diluted supernatants from these colonies are used to infect NIH 3T3 cells; a high titer LXSN virus is used as a control. Southern blot hybridizations with an LX specific probe identify supernatants that efficiently transduce intact copies of the retrovirus to 90–100% of the cultured cells.

If desired, before transfecting retroviral DNAs into packaging cell lines, the constructs may be tested for expression in 16 day fetal liver of transgenic mice as described by Ryan et al. (Genes Dev. 3:314–323, 1989). Constructs that are expressed at a high level are used to produce virus for bone marrow infections.

When a packaging cell line that produces high titer virus (preferably, $10^6$/ml) is obtained, bone marrow from Hb S mice is infected; production of such Hb S mice is carried out as described above using mutant Hb S hemoglobin transgenes (see, e.g., Ryan et. al., Science 247:566–568, 1990). To facilitate infection, bone marrow from Hb S mice are co-cultured with the packaging line in the presence of IL-3 and IL-6 (Bodine et al., Proc. Natl. Acad. Sci. USA 86(22) :8897–901, 1989). After 48 hours, cells are injected via the tail vein into recipient Hb S animals that have been lethally irradiated. After a one month recovery period, small aliquots of blood are removed and hemoglobins are analyzed on native IEF gels and denaturing cellulose acetate strips (see, e.g., Behringer et. al., Science 245:971–973, 1989. Preparative IEF was performed on 4% acrylamide gels with 2% Pharmalyte pH 6.7 to 7.7. Bands of hemoglobin were sliced from the gel and eluted in 0.1M potassium phosphate buffer, pH 7.0). When animals that express human β-globin at approximately 20% of total β-globin are obtained, solubility assays are performed to quantitate anti-sickling activity. Also, erythrocytes from these animals are deoxygenated and examined for sickled forms. Results are compared to control animals that have been transplanted with Hb S marrow infected with LXSN virus only.

Mutant hemoglobins shown to inhibit sickling in Hb S mice are then included in the appropriate mammalian retroviral vector and introduced into a mammal of choice, generally as described above. Retroviral vectors, or other viral vectors with the appropriate tropisms for blood cells, may be used as gene transfer delivery systems for the anti-sickling hemoglobin gene. Numerous vectors useful for this purpose are generally known and have been described (see for example, Miller, Human Gene Therapy 1:5–14, 1990; Friedman, Science 244:1275–1281, 1989; Anderson, Science 256:808–813, 1992; Eglitis et al., BioTechniques 6:608–614, 1988; Tolstoshev et al., Current Opinion in Biotechnology 1:55–61, 1990; Cornetta et al., Nucleic Acid Research and Molecular Biology 36:311–322, 1987; Anderson, Science 226:401–409, 1984; Moen, Blood Cells 17:407–416, 1991; and Miller et al., Biotechniques 7:980–990, 1989). Retroviral vectors are particularly well developed and have been used in a clinical setting (see, for example, Rosenberg et al., N. Engl. J. Med. 323:370, 1990). Preferably, the anti-sickling hemoglobin genes are introduced by retroviral transfer into a sample of a patient's bone marrow stem cells (also as described herein and in Miller, 1990, supra; Friedman, 1989, supra; Anderson, 1992, supra; Eglitis et al., 1988, supra; Tolstoshev et al., 1990, supra; Cornetta, 1987, supra; Anderson, 1984, supra; Moen, 1991, supra; Miller et al., 1989, supra; and, Rosenberg et al., 1990, supra).

Example: Characterization of anti-sickling hemoglobins AS1 and AS2 produced in transgenic mice Transgenic lines expressing AS1 or AS2 were established, and hemolysates obtained from several animals were analyzed by anion exchange high performance liquid chromatography (HPLC) to quantitate the amounts of human, mouse, and hybrid hemoglobins (Ip et al., Anal. Biochem. 156:348, 1986; Hemoglobin tetramers were separated by anion exchange HPLC utilizing a Synchropak AN 300 (4.6 mm×25 mm) column (SynChrom, Lafayette, Ind.)). FIGS. 5A and 5C show that 28% of total hemoglobin was Hb AS1 in one $\alpha\beta^{AS1}$ transgenic line, and 18% of total hemoglobin was Hb AS2 in one $\alpha\beta^{AS2}$ transgenic line. Hemoglobins AS1 and AS2 were isolated by preparative IEF (Behringer et al., Science 245:971, 1989) and the purity of the human hemoglobins was assessed by denaturing reverse phase (HPLC) which separates the α- and β-globin subunits (Adachi et al., J. Chromat. 419:303, 1987. Mouse and human globins were separated by RP-HPLC using a Dionex Series 4500i HPLC system (Sunnyvale, Calif.). Approximately 25–30 μg of hemoglobin was injected into a Vydac C4 reversed phase column (4.6 mm×250 mm; Hibernia, Calif.) and eluted with a linear gradient of acetonitrile and 0.3% trifluoroacetic acid as described in Shelton et al., J. Liq. Chrom. 7:1969, 1977). FIGS. 5B and 5D show that Hb AS1 was approximately 90% pure, while Hb AS2 was purified to homogeneity.

The oxygen equilibrium curves (OEC) for purified Hb AS1 and Hb AS2 are illustrated in FIGS. 6A and 6C (Asakura et al. in *Oxygen Transport in Red Blood Cells,* C. Nicolau Ed. (Pergamin, N.Y., 1986). Oxygen equilibrium curves were measured with a Hemox Analyzer (TCS, Southampton, Pa.). The OEC were determined in 0.1M potassium phosphate buffer, pH 7.0 at 20° C.). These sigmoidally shaped curves demonstrate the normal cooperativity of oxygen binding (FIGS. 6A and 6C). The $P_{50}$ value, which measures the partial pressure of oxygen at which hemoglobin is half-saturated, was determined for Hb AS1 and Hb AS2 and compared with Hb A and Hb F (Table 1). The $P_{50}$ for Hb AS1 is slightly elevated, but within the normal range, and this hemoglobin responds normally to the allosteric effector 2,3-diphosphoglycerate (2,3-DPG); that is, oxygen affinity is decreased in the presence of 2 mM 2,3-DPG (FIG. 6B). The $P_{50}$ for Hb AS2 is slightly lower than normal (6.7 mm Hg) but 2,3-DPG raises this value to 8.4 mm Hg. The oxygen affinity of Hb AS2 is functionally equivalent to Hb F in the presence of 2 mM 2,3-DPG (FIG. 6D) and, therefore, Hb AS2 should adequately bind and deliver oxygen in vivo.

TABLE 1

$P_{50}$ values for recombinant and naturally-occurring human hemoglobins

| | $P_{50}$ (mm Hg) | |
|---|---|---|
| Sample | without DPG | with DPG |
| Hb AS1 | 10.5 | 15.0 |
| Hb AS2 | 6.7 | 8.4 |
| Hb A | 8.7 | 13.3 |
| Hb F | 8.8 | 10.0 |

Anti-sickling Properties of AS1 and AS2 hemoglobins

Hb S (100%) or mixtures of Hb S (75%) and Hb A, AS1, AS2, or F (25%) were deoxygenated and polymerization as a function of time was measured spectrophotometrically as the temperature of the hemoglobin solution was raised from 0° C. to 30° C. (Adachi et al., J. Biol. Chem. 254:7765, 1979; Adachi et al., J. Biol. Chem. 255:7595, 1980; Kinetics of polymerization were determined in 1.8M potassium phosphate buffer. Polymerization was initiated using the temperature jump method in which the temperature of deoxygenated hemoglobin solutions is rapidly changed from 0° C. to 30° C. and the time course of aggregation is monitored turbidimetrically at 700 nm). FIG. 7A shows that Hb S polymerizes relatively rapidly and that Hb A, AS1, AS2, and F delay Hb S polymerization to different extents. Hb AS1 inhibits Hb A polymerization more efficiently than Hb A; however, Hb AS1 inhibits much less effectively than Hb F which is known to inhibit sickling in vivo at a 3:1 ratio (Noguchi et al., New Eng. J. Med. 318:96, 1988). Finally, Hb AS2 inhibits Hb S polymerization at approximately the same level as Hb F. This result strongly suggests that Hb AS2 will inhibit Hb S polymerization in vivo if expression of AS2 at a level of 25% of total hemoglobin can be achieved.

The delay times determined in FIG. 7A were all measured at a concentration of 60 mg/dl. FIG. 7B shows the results of similar experiments performed at variable concentrations of total hemoglobin. The ratio of Hb S to Hb A, AS1, AS2 or F in all of these experiments was 3:1. In this figure the log of the reciprocal of the delay time and the log of hemoglobin concentration are plotted. As reported previously (Hofrichter et al., Proc. Natl. Acad. Sci. USA 71:4864, 1974; Wishner et al., J. Mol. Biol. 98:179, 1975; Crepeau et al., Nature 274:616, 1978; Dykes et al., J. Mol. Biol. 130:451, 1979; Padlan et al., J. Biol. Chem. 260:8280, 198; and Eaton et al., Blood 70:1245, 1987), an empirical relationship between delay time and hemoglobin concentration can be described by the following equation: $1/td=\gamma S^n$, where S=[Hb]total/[Hb]soluble, and $\gamma$ is an experimental constant. The n value is related to the size of nuclei formed during polymerization. The n values of the data shown in FIG. 7B are between 2 and 3, which agree well with those shown previously in high phosphate buffer (Adachi et al., J. Biol. Chem. 254:7765, 1979). At higher concentrations of hemoglobin, the delay times for Hb AS2 and Hb F overlap, indicating that Hb AS2 and Hb F have virtually identical anti-polymerization activity.

The results described above demonstrate that the genetic modification of two surface amino acids in Hb A produces a unique human hemoglobin (Hb AS2) that inhibits Hb S polymerization as effectively as Hb F. As discussed above, the β-globin LCR enhances β-globin gene expression much more effectively than γ-globin gene expression in adult erythroid cells. Therefore $\beta^{AS2}$, which is a β-globin gene with the anti-polymerization properties of γ-globin, a useful molecule for future genetic therapy of sickle cell disease.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A recombinant human β-globin with anti-sickling activity, said recombinant human β-globin having amino acid substitutions in amino acid positions 22 and 80.

2. The recombinant human β-globin of claim 1, comprising alanine at amino acid position 22.

3. The recombinant human β-globin of claim 1, comprising lysine at amino acid position 80.

4. The recombinant human β-globin of claim 1, comprising alanine at amino acid position 22 and lysine at amino acid position 80.

5. A recombinant human β-globin with anti-sickling activity, said recombinant human β-globin having amino acid substitutions in amino acid positions 22 and 87.

6. The recombinant human β-globin of claim 5, comprising alanine at amino acid position 22.

7. The recombinant human β-globin of claim 5, comprising glutamine at amino acid position 87.

8. The recombinant human β-globin of claim 5, comprising lysine at amino acid position 87.

9. The recombinant human β-globin of claim 5, comprising alanine at amino acid position 22 and glutamine at amino acid position 87.

10. The recombinant human β-globin of claim 9, further comprising an amino acid substitution at amino acid position 16.

11. The recombinant human β-globin of claim 10, comprising aspartic acid at amino acid position 16.

12. The recombinant human β-globin of claim 5, comprising alanine at amino acid position 22 and lysine at amino acid position 87.

13. The recombinant human β-globin of claim 12, further comprising an amino acid substitution at amino acid position 16.

14. The recombinant human β-globin of claim 13, comprising aspartic acid at amino acid position 16.

15. The recombinant human β-globin of claim 5, further having an amino acid substitution at amino acid position 16.

16. The recombinant human β-globin of claim 15, comprising aspartic acid at amino acid position 16.

* * * * *